US006971983B1

(12) United States Patent  (10) Patent No.: US 6,971,983 B1
Cancio  (45) Date of Patent: Dec. 6, 2005

(54) THERAPEUTICALLY BENEFICIAL MOVABLE MAGNETIC FIELDS

(76) Inventor: Humberto Cancio, 7731 SW. 32 St., Miami, FL (US) 33155

( * ) Notice: Subject to any disclaimer, the term of this patent is extended or adjusted under 35 U.S.C. 154(b) by 0 days.

(21) Appl. No.: 10/885,158

(22) Filed: Jul. 6, 2004

(51) Int. Cl.$^7$ ................................................ A61N 2/00
(52) U.S. Cl. ........................................................ 600/9
(58) Field of Search ....................................... 600/9–15

(56) References Cited

U.S. PATENT DOCUMENTS

| | | | |
|---|---|---|---|
| 4,537,181 A * | 8/1985 | Shalhoob et al. ............... | 600/9 |
| 4,727,857 A * | 3/1988 | Horl .............................. | 600/15 |
| 4,744,350 A | 5/1988 | Sato | |
| 5,084,003 A | 1/1992 | Susic | |
| 5,453,073 A * | 9/1995 | Markoll ........................ | 600/14 |
| 5,632,720 A | 5/1997 | Kleitz | |
| 5,667,469 A * | 9/1997 | Zhang et al. ................... | 600/9 |
| 5,788,624 A | 8/1998 | Lu et al. | |
| 5,817,000 A | 10/1998 | Souder | |
| 6,001,055 A | 12/1999 | Souder | |
| 6,231,497 B1 | 5/2001 | Souder | |
| 6,663,557 B2 * | 12/2003 | Werny ........................... | 600/15 |
| 2004/0097781 A1 * | 5/2004 | Ichikawa et al. ............... | 600/9 |

* cited by examiner

*Primary Examiner*—John P. Lacyk
(74) *Attorney, Agent, or Firm*—Malloy & Malloy, P.A.

(57) ABSTRACT

The present invention relates to a therapeutically beneficial assembly utilizing one or more moveable magnetic fields passing through a treatment area, which is dimensioned and configured to accommodate a user in a standing, walking and/or running orientation therein. A generating assembly comprises at least one but preferably at least two magnetic arrays each mounted in moveable relation to the treatment area and comprising a conveyor-like base having a plurality of magnets connected thereto and moveable therewith. The plurality of magnets of each of said magnetic array are disposed to generate a different magnetic field moveable through said treatment area such that the user therein is exposed to the one or more moveable magnetic fields.

33 Claims, 3 Drawing Sheets

THERAPEUTICALLY BENEFICIAL MOVABLE MAGNETIC FIELDS

BACKGROUND OF THE INVENTION

1. Field of the Invention

This invention relates to an assembly for generating one or more movable magnetic fields which communicate with a treatment area and a user therein. The treatment area is structured to allow the user to assume an upright, standing, walking or running orientation and receive therapeutic benefit by being exposed to the magnetic fields continuously passing through the treatment area.

2. Description of the Related Art

It has long been recognized and generally well-settled that exposing the body of both humans and animals to a magnetic field offers some therapeutic benefits. Clearly, it has been established that the bodies of animals, including humans, are capable of conducting electricity. As such, a variety of healthcare treatments, methods and devices incorporating the use of magnetic fields have been devised and tested. In years past for example, it was even believed that the health of sailors who traveled across the seas in wooden ships was improved, due at least in part, to exposure to the earth's magnetic field, especially when ships traveled in either an easterly or westerly direction.

Known, modern day applications of magnetism and/or the generation of magnetic fields includes devices which allow a magnetic flux to penetrate into the body typically at predetermined localized areas. More specifically, magnetic devices and structures intended for therapeutic use include watches, rings, bracelets, vests, belts, shoes and a variety of other articles. In addition, furniture and body support devices such as cushions, mattresses, beds, etc. have also been utilized in combination with magnets. Common to most, if not all, of the above-noted category of magnetic devices is the incorporation of one or more magnets located in a position or orientation which facilitates the exposure of a specific body portion of an individual to a substantially stationary magnetic field.

Assuming that magnetic treatment of the type set forth above does have therapeutic value and benefits, there are continuing questions relating to the significance of such therapeutic benefits, especially when only a localized area or body portion is being exposed to a magnetic field or magnetic flux. It has further been suggested that devices worn on the body of individuals may, in fact, result in certain harmful effects such as swollen or irritated joint areas such as the wrist, finger joints, etc.

Perhaps even more questionable, is the use of magnetically treated products which are intended to be orally consumed, such as magnetized drinking water. It is suggested that the practice of consistently drinking water that has been magnetized may have some effect in the prevention and treatment of certain ailments. It is believed that the therapeutic benefits associated therewith are limited due to the rapid passage or circulation of the water through the body. As a practical matter, the effect of magnetizing drinking water after a certain period of time is significantly lessened.

In order to overcome many, if not all, of the disadvantages and problems associated with both localized magnetic devices and consumable magnetized products, it is suggested by the inventor hereof that exposing animals, including humans, to a continuously moving magnetic field, may provide a longer lasting and overall greater therapeutic benefit to those individuals who are exposed, even if for relatively brief time periods. Further, if any such system or assembly were developed that incorporates the use of one or more moving magnetic fields, it would be preferable if it were applied and/or structured such that a user or individual being treated is in an upright position, and ideally, if while so oriented the treated individual may even exercise, i.e., be involved in a prescribed or selective movement such as walking, running, jogging, etc. In this manner, any disadvantages associated with magnetic devices intended to treat localized areas such as bracelets, rings, shoes, etc. would be overcome through the application of one or more magnetic fields which preferably pass through a treatment area in which the treated individual is walking, jogging or at least oriented in an upright position. Further, if any such system or assembly were developed that incorporates the use of one or more moving magnetic fields, it would be preferable if it also offers an ability to adjust the physical and operative characteristics of the generated magnetic fields to allow increased areas of the torso, legs, arms, etc. to be exposed during the continuous and/or other predetermined movement of the generated magnetic fields as they pass through the treatment area. In addition, if any such improved assembly were developed, it would also preferably be structured to expose a user to one or more therapeutically beneficial magnetic fields structured to have sufficient versatility in its application to enable its use by individuals of all ages and sizes.

SUMMARY OF THE INVENTION

The present invention is directed to an assembly structured to generate one or more movable magnetic fields and expose a user thereto, while the user is within an at least partially defined treatment area. Further, the assembly of the present invention comprises a generating assembly structured to generate the one or more magnetic fields such that the magnetic fields move through the treatment area and expose the user therein to the therapeutic benefits created thereby. Accordingly, the assembly of the present invention is intended to overcome many if not all of the disadvantages and problems associated with the conventional devices or assemblies which attempt to localize a magnetic field relative to a certain portion of an individual's body.

In contrast, the magnetic fields produced by the generating assembly of the various preferred embodiments of the present invention are maintained, while in use, in substantially continuous motion. Further the generated magnetic fields pass through the treatment area in a predetermined manner so as to expose substantially the entire torso and/or other portions of a user's body thereto in a manner intended to maximize the therapeutic benefits.

More specifically, the assembly of the present invention, and at least some of the preferred embodiments thereof, comprise a frame disposed adjacent to and at least partially defining the treatment area. The frame and accordingly the treatment area is dimensioned, configured and otherwise structured to facilitate the user assuming an upright position. While the user is so disposed, the one or more generated magnetic fields move through the treatment area preferably, but not exclusively, in a somewhat transversely oriented direction so as to expose major or predetermined portions of the users torso to the magnetic fields.

In addition one or more additional preferred embodiments of the present invention incorporate the use of a support platform disposed within the treatment area in supporting relation to the user. The support platform may be structured to facilitate movement of the user, at least to the extent of the user assuming a walking or running orientation as desired. By way of example only, the moveable support platform may comprise a treadmill assembly. Therefore, practical application of the present invention may include concurrent movement of the user within the treatment area while being exposed to the one or more movable magnetic fields. In yet another preferred embodiment of the present invention, the aforementioned moving orientation of the user, while in the treatment area, may be accomplished by providing the frame with a moveable support assembly. As such, the moveable support assembly is structured to allow movement of the frame and accordingly the treatment area over a supporting surface. The force required to move the frame and treatment area may be supplied by the user walking or running along the supporting surface while pushing or otherwise propelling the frame. This latter described preferred embodiment would eliminate the need of a movable support platform, such as a treadmill assembly, as described above.

The generating assembly comprises at least one but preferably a plurality of at least two magnetic arrays movably mounted adjacent the treatment area and in communication therewith. In a most preferred embodiment, each of the magnetic arrays are movably connected to the frame in predetermined relation to one another and to the treatment area. When so disposed, the respective magnetic fields generated by the magnetic arrays will be directed inwardly towards the interior of the treatment area and the user disposed therein. Each of the magnetic arrays comprises a plurality of magnets disposed in predetermined relation to one another and collectively mounted on a moveable base.

While the plurality of magnets and the base may assume a variety of different structural and operative configurations, one preferred embodiment includes the base being in the form of a continuously configured conveyor structure movable along a continuous, closed path of travel. When activated, the base is maintained in continuous motion such that the plurality of magnets associated therewith generate a magnetic field which, as set forth above, passes through the treatment area so as to expose major and/or predetermined portions of a user's body thereto. Also, in order to accomplish the desired therapeutic benefit, two of the magnetic arrays are disposed on opposite sides of the frame, the treatment area and the user disposed therein. Also, when the magnetic arrays include the base comprising a continuously movably conveyor-type structure, as set forth above, they may preferably be disposed to effectively rotate or move in opposite directions. Accordingly, the user, who is in the middle of both magnetic arrays, experiences a movement of the magnetic flux in essentially only one continuous direction as the magnetic arrays and the generated magnetic fields move in a single direction along a substantially linear path of travel relative to and through the treatment area. As a result a user within the treatment area is exposed to at least two continuously moving magnetic fields passing through the treatment area on opposite sides of the user and in a common direction.

Optimal conditions to accomplish the maximum therapeutic value of the generated magnetic fields may involve the synchronized movement of the two magnetic arrays as well as the cooperative orientation of the plurality of magnets on each of the movable bases. Moreover, the plurality of magnets associated with each of the magnetic arrays may vary in structure, size, configuration and operation. As such, each of the plurality of magnets may be permanent magnets, wherein the respective poles thereof are cooperatively positioned relative to the remaining plurality of magnets associated with the same magnetic array. Predetermined and/or selective positioning of the plurality of magnets and the base associated therewith serve to produce a magnetic field of predetermined size, configuration and disposition. Also, a selective or predetermined variation of the magnetic field may be created in order to add significant versatility to the exposure of the user to the continuously moving magnetic fields, while in an upright orientation in the aforementioned treatment area.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying drawings, the present invention is directed to an assembly generally indicated as 10 structured to expose a user, generally indicated as 12, to one or more moving magnetic fields for the purpose of gaining the therapeutic benefits and/or potentially curative properties thereof. With primary reference to FIG. 1, one preferred embodiment of the assembly of the present invention includes a frame generally indicated as 14. The frame 14 is dimensioned, configured and has an overall structure to at least partially define a treatment area generally indicated as 16. The treatment area 16 is such as to allow the user 12 to assume an upright orientation. As will be explained hereinafter, with reference to additional preferred embodiments, the frame and treatment area are further structured to allow the user 12 to assume a walking, jogging, or running orientation concurrently to being exposed to the one or more moving magnetic fields.

Figure 1:
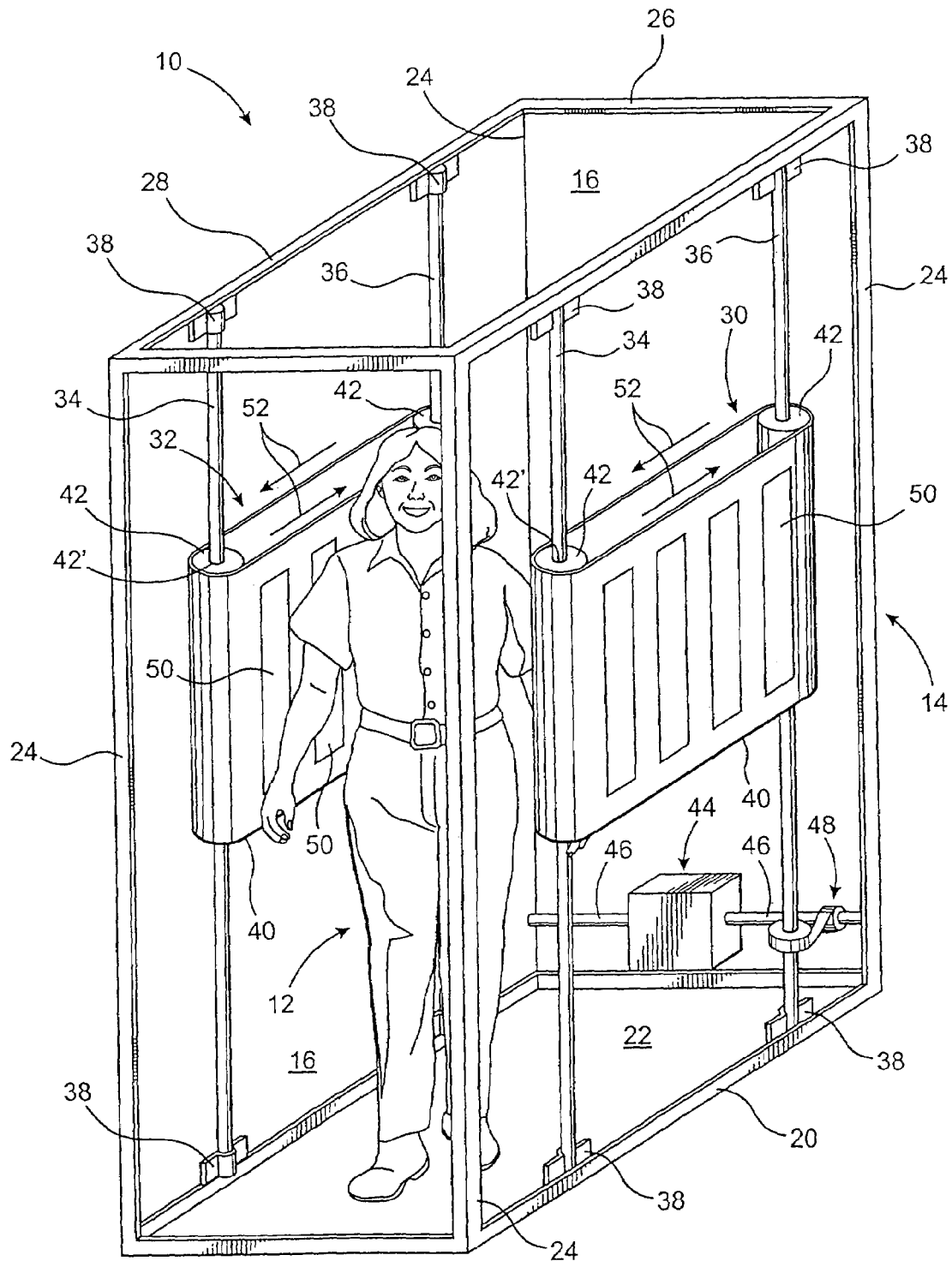
FIG. 1 is a perspective view of the assembly of the present invention structured to include a plurality of generating assemblies each of which are structured to generate separate but cooperative magnetic fields to which a user is exposed while in a treatment area.

It is emphasized that the frame 14 may assume a plurality of different structures, dimensions and configurations, any of which are capable of at least partially defining the treatment area 16 which enables the user 12 to assume the aforementioned upright stationary or moving orientation. Accordingly, by way of example, the preferred embodiment of the frame 14 as represented in FIG. 1 includes a bottom section 20 disposed in somewhat surrounding relation to a support platform 22. The support platform 22 may be defined by the floor or ground surface on which the frame 14 is disposed, in which case the bottom frame portion 20 is open. Alternatively, the support surface 22 may comprise a separate flooring or platform structure connected to or otherwise associated with the frame 14.

In addition, the frame 14 preferably includes a plurality of vertically or otherwise oriented upright stanchions 24 connected to the bottom frame portion 20 and extending upwardly therefrom. An upper frame portion 26 may be disposed and configured to define the periphery of an upper opening 28 communicating directly with the interior of the frame 14 and/or the treatment area 16. Another structural modification of the frame 14 may be the enclosure of the opening 28 by means of one or more covering panels. Similarly the various side portions of the frame 14 disposed between the upright stanchions 24 are preferably open but may be at least partially enclosed by one or more panels or panel segments. When fully or at least partially enclosed, the enclosing panels or panel segments may be formed from transparent, translucent or opaque materials. The openly configured frame 14 of course provides the advantage of having a free circulation of ambient air passing through the treatment area 16 as well as facilitating visual access to and by the user 12 during a treatment procedure.

The aforementioned one or more moving magnetic fields are established by a generating assembly comprising at least one magnetic array generally indicated as 30 and more practically a plurality of at least two magnetic arrays such as 30 and 32. In the preferred embodiment of FIG. 1, each of the magnetic arrays 30 and 32 are located adjacent the treatment area 16 so as to provide correspondingly generated magnetic fields which communicate directly with the interior of the treatment area 16 and the user 12 therein. Also, each of the magnetic arrays 30 and 32 may be connected to the frame 14 or be otherwise mounted immediately adjacent thereto and preferably on opposite sides of the treatment area 16 as demonstrated. When connected directly to the frame 14, each magnetic array 30 and 32 may include spaced apart support rods 34 and 36 attached to the frame 14 by journal or bearing assemblies 38 located at opposite ends of the support rods 34 and 36. The journal or bearing assemblies 38 serve to fixedly or rotationally connect the respective support rods 34 and 36 to the lower frame portion 20 and the upper frame portion 26.

In addition to the above, each of the magnetic arrays 30 and 32 include a base 40 preferably, but not necessarily, in the form of a conveyor structure having a closed or continuous configuration. Each of the bases 40 are interconnected to and between the support rods 34 and 36 by rollers or equivalent structures as at 42. Moreover, each base 40 is interconnected by appropriate linkage to a driving assembly, generally indicated as 44. The drive assembly 44 may be in the form of an electrically or otherwise powered drive motor having one or more power take-off shafts 46 interconnected by appropriate linkage 48 to at least one of the support rods, as at 36. Activation of the drive assembly 44 causes a driving rotation of both of the power take-off shafts 46 and concurrent rotation of at least one of the support rods 36, associated with each base 40, by means of the interconnecting linkage 48. As one example of the structure and function of the embodiment of FIG. 1, one of the rollers 42 may be fixedly connected to and rotate with the corresponding support rod 36, wherein the opposite roller 42 may be interconnected to the support rod 34 by means of a bearing assembly 42'. Therefore continuous operation of the drive motor/drive assembly 44 will cause a continuous rotation of each of the support rods 36 and corresponding rollers 42. Concurrently the support rods 34 will remain fixed while the rollers 42 associated therewith will be allowed to rotate, because of their attachment to the support rods 34 by bearing structures 42'. A continuous rotation of conveyor-like bases 40 will result in the production of continuously moving magnetic fields as will be explained in greater detail hereinafter.

Figure 3:
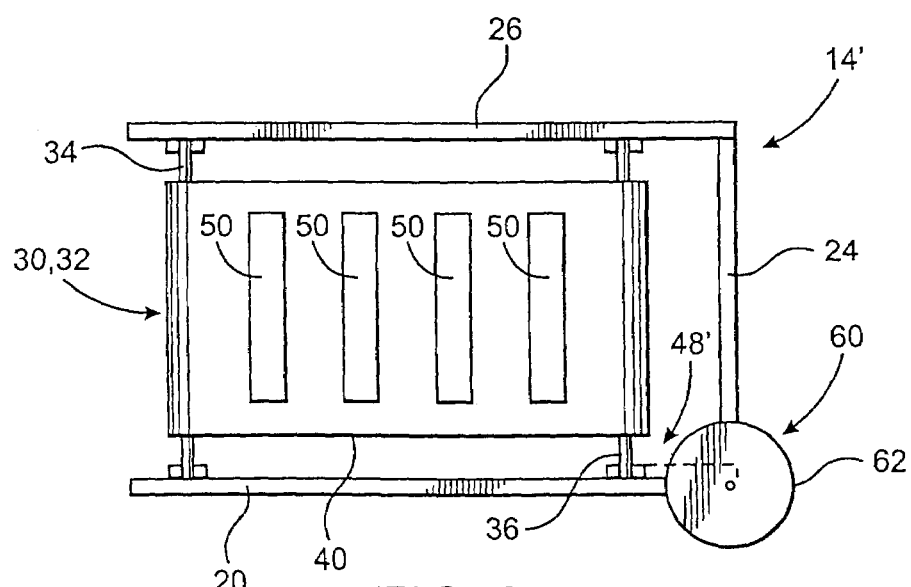
FIG. 3 is a side view in partial cutaway including at least one generating assembly similar to that represented in the embodiment of FIG. 1 but clearly adaptable to the embodiment of FIG. 2.

As clearly represented in FIGS. 1 and 3 each of the magnetic arrays 30 and 32 include a plurality of magnets 50 mounted on the exterior face of and moveable with corresponding ones of the bases 40. When the drive assembly 44 is activated, the bases 40 rotate, preferably in a predetermined single, common, linear direction as they pass along opposite sides of the treatment area 16, such as that indicated schematically by the directional arrows 52. The plurality of magnets 50 may comprise permanent magnets disposed in spaced relation to one another along the length of the outer face of the base 40 and are preferably sufficient in number to collectively cover substantially the entire length of the outer face or at least a predetermined majority of the length thereof. The plurality of magnets 50 may differ in number, size, configuration, etc. to accomplish the primary purpose of generating a magnetic field. As should be apparent the cooperative disposition of each of the plurality of magnets 50 associated with the different magnetic arrays 30 and 32 are such that the different magnetic fields generated thereby pass in a single substantially linear direction or along a linear path of travel through the treatment area 16, as also indicated by directional arrow 52 while exposing user 12 thereto.

While the plurality of magnets 50 are initially described as being permanent magnets, it is intended that the spirit and scope of the present invention also include the plurality of magnets 50 being defined by electromagnets. When so structured, the various poles and the resulting magnetic flux generated by each of the electromagnets 50 may be varied by regulating current flow thereto. Regardless of the structuring of the plurality of magnets 50 being either permanent or electromagnets, the intensity of the generated magnetic flux must be sufficient to expose the user 12, when located within the treatment area 16, to the continuously moving magnetic fields generated by each of the magnetic displays 30 and 32.

Accordingly, the disposition of the plurality of magnets 50, the movement of the individual bases 40 and the resulting magnetic fields generated thereby may be synchronized. As indicated, such synchronization may be accomplished by current flow regulation to the plurality of magnets 50, when such are electromagnets. Also, the operation of the drive assembly 44, the location and structure of the power take-off shafts 46 and the location and operation of the interconnecting linkage 48 may also serve to accomplish a predetermined synchronization of the moving magnetic fields. As generally shown in FIG. 1 and described above, an appropriate interconnecting linkage 48 also serves to drivingly interconnect a corresponding one of the power take-off shafts 46 with the support rod 36 associated with the magnetic array 32.

Figure 2:
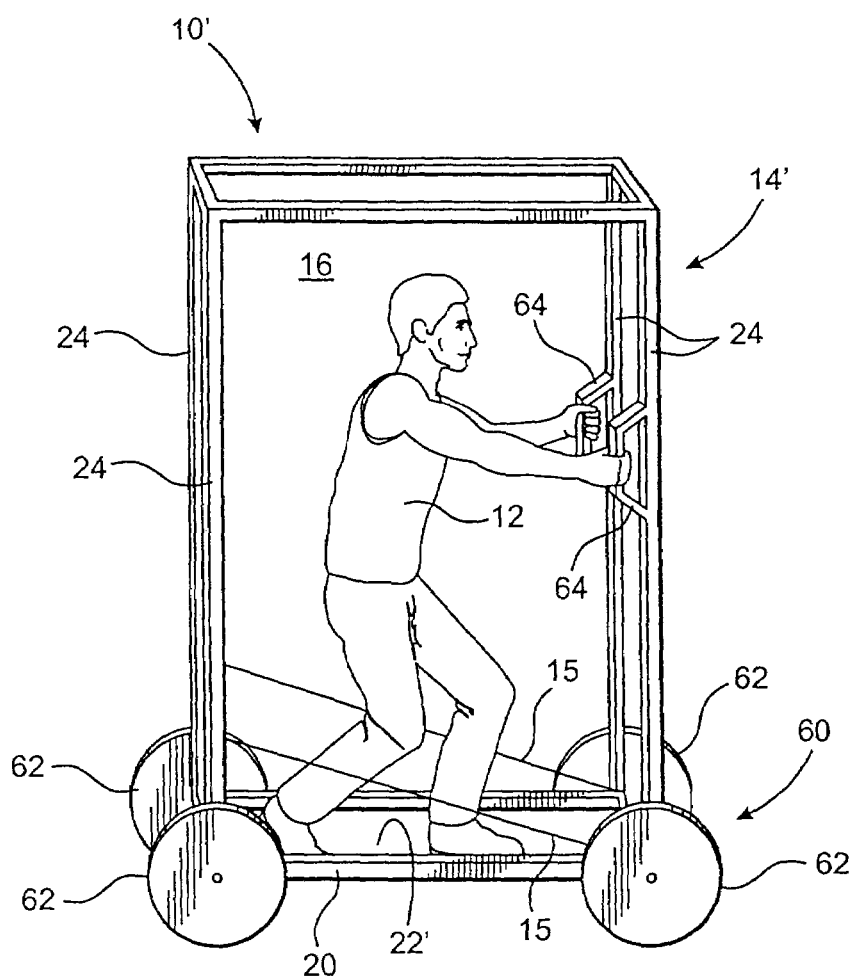
FIG. 2 is a perspective view of yet another preferred embodiment of the assembly of the present invention.

Yet another preferred embodiment of the present invention is represented in FIGS. 2 and 3. Moreover, a frame 14' at least partially establishes or defines the boundaries of the treatment area 16 so as to allow the user 12 to maintain the preferred upright position. The structural and functional features of the frame 14' are such as to facilitate the user assuming a walking, jogging and/or running orientation, while in the upright position as demonstrated. More specifically, the frame 14' includes a movable support assembly generally indicated as 60, including a plurality of wheels, rollers, or other appropriate movable support structure 62 connected to the lower portion 20 of the frame 14'. As such, the frame 14' is mobile and is powered by the walking, jogging, running, etc. motion of the user 12, while exerting a pushing or other appropriate force on the frame 14'. Gripping handles or other appropriate structures 64 are provided for this purpose. Concurrently to exerting the propelling force on the frame 14', the user 12 moves across the support surface 22' on which the frame 14 and the movable support assembly 60 are positioned. Therefore, the lower portion 20 of the support frame 14 is open to allow the feet of the user 12 to engage the supporting surface 22', which may be flooring, ground surface, etc. Additional cross braces 15 may be added to the frame 14' for purposes of maintaining a sufficient structural integrity of the frame 14', which may be required due to the forced movement thereof as the user 12 across the support surface 22'.

While not specifically represented in FIG. 2, frame 14' includes at least one but preferably a plurality of two magnetic arrays 30 and 32 located on opposite sides of the frame 14' similar to that demonstrated in the preferred embodiment of FIG. 1. As with each of the magnetic arrays 30 and 32 of the embodiment of FIG. 1, the same or appropriately equivalent magnetic arrays 30 and 32 are demonstrated in FIG. 3 and include a movable base 40 and a plurality of magnets 50 as previously discussed. However, one distinguishing feature of the embodiment of FIGS. 2 and 3 is the forced, driving rotation of each of the plurality of magnetic arrays 30 and 32 by the manually powered movement of the frame 14'. More specifically, rotation of the movable support assembly 60 including one or more of the wheels or other moveable support member 62 causes driving rotation of each of the support shafts 36 through appropriate interconnecting linkage 48'. As schematically represented the linkage 48' is disposed in driving interconnection between the movable support assembly 60 and each of the support rods 36 associated with each of the magnetic arrays 30 and 32. It should be apparent that any of a variety of different gearing, drive belts, chain drives or mechanical linkage may define the interconnecting linkage 48'.

Figure 4:
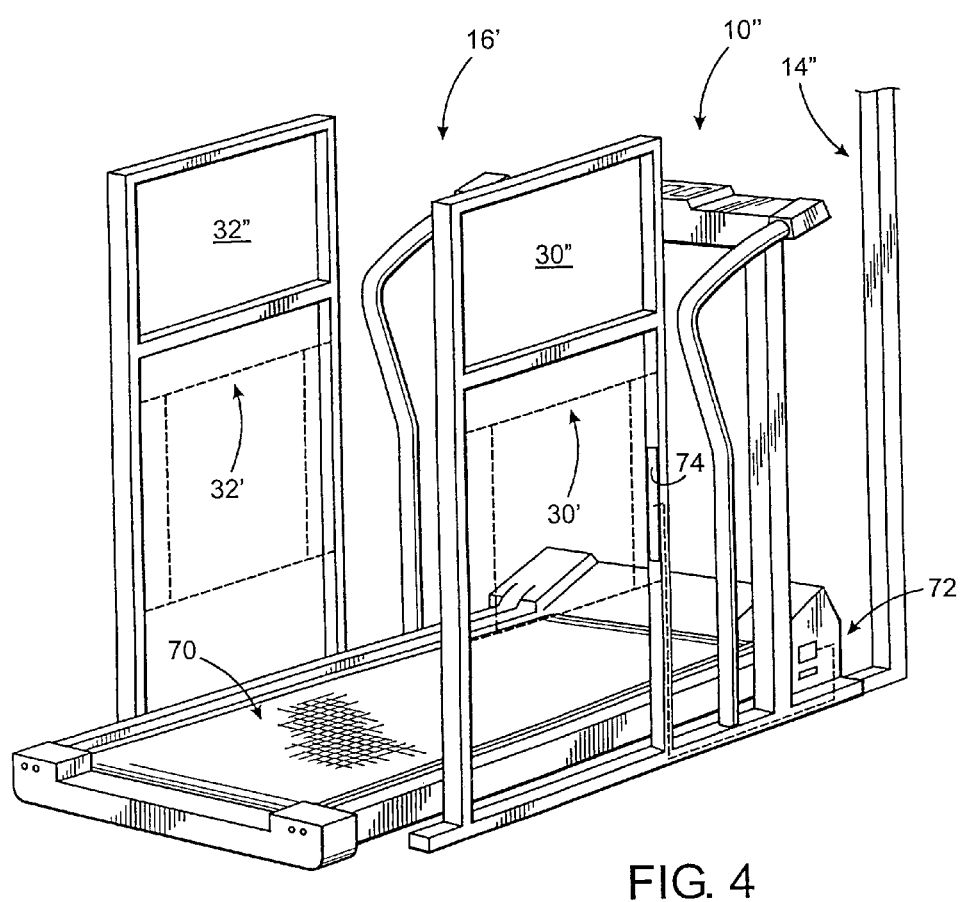
FIG. 4 is a perspective view in partial cutaway of yet another preferred embodiment of the present mentioned incorporating a movable support platform within a treatment area.
Figure 1:
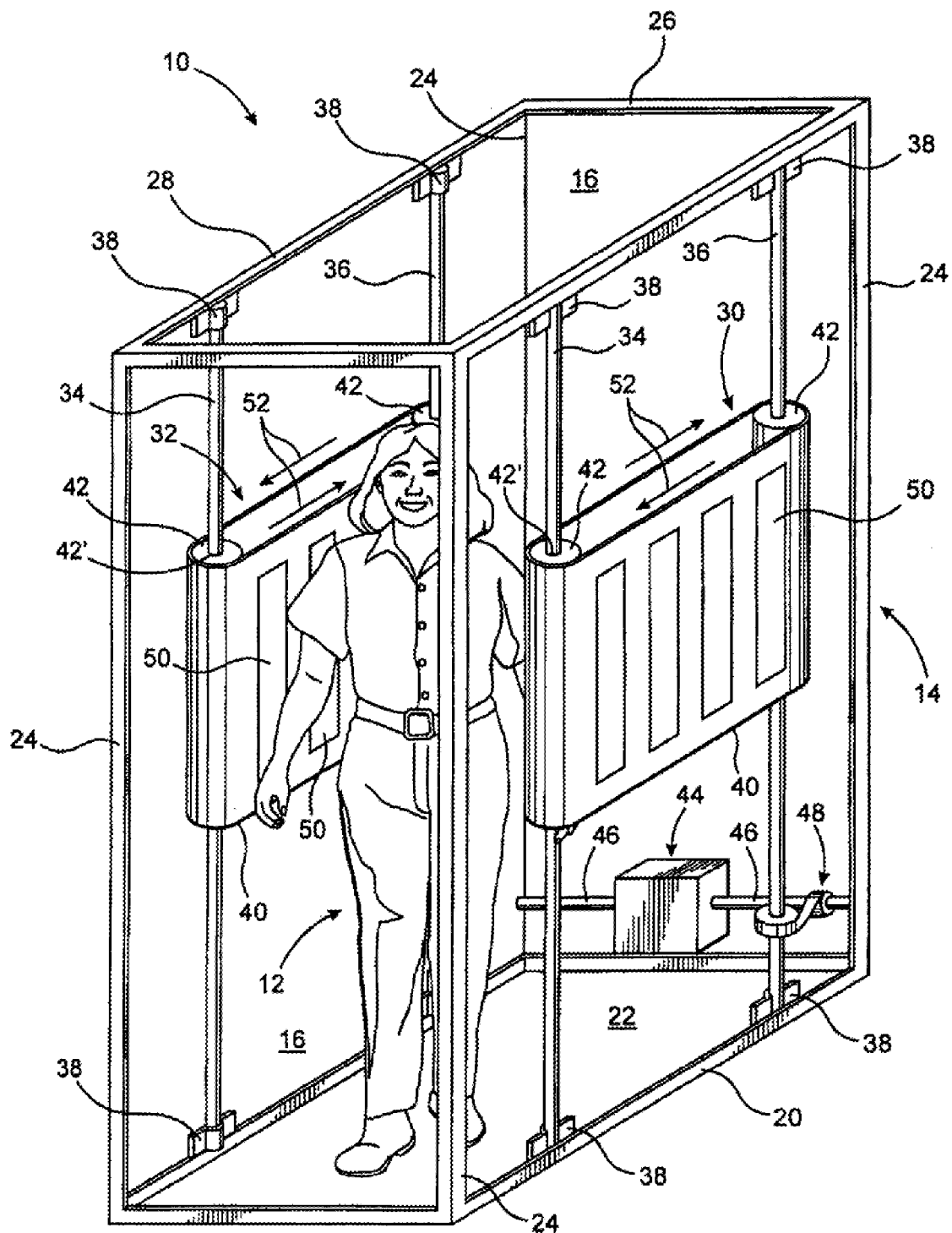

Yet another embodiment of the present invention is represented at least partially in schematic form in FIG. 4. More specifically the assembly 10" includes the frame 14" shown in partial cutaway and disposed in at least partially surrounding relation to the treatment area 16. Also located within the treatment area 16 is a support platform 70 which is specifically structured to facilitate walking, jogging, running, etc. of a user 12 while supported thereon. As should be apparent the preferred embodiment of FIGS. 2 and 3 define the treatment area 16 movable with the mobile frame 14'. To the contrary, in the preferred embodiment of FIG. 4, the treatment area 16 more closely resembles the treatment area 16 of the embodiment of FIG. 1 at least to the extent that the treatment area 16 and the frame 14" are intended to be stationary.

As such, a user 12 may be within the treatment area 16 in an upright position and when so disposed, the user 12 is supported on the movable support platform 70. The moveable support platform preferably, but not exclusively, comprises a treadmill assembly or other structure which electrically/mechanically operates to allow movement of the user 12 in a walking, running, jogging orientation. Also schematically represented is the inclusion of a generating assembly having at least one, but preferably a plurality of two magnetic arrays 30' and 32'. As with the embodiments of FIGS. 1 through 3, the magnetic arrays 30' and 32' are located on opposite sides of the treatment area 16 and a user 12 disposed therein. Accordingly, during walking, running, and/or jogging-type movement while supported on the movable support platform 70, the user is also being concurrently exposed to the different magnetic fields generated by the magnetic arrays 30' and 32'. The continuous movement of the one or more magnetic arrays 30', 32' may be accomplished by a power take-off assembly, generally indicated as 72, being connected to the driving mechanism of the treadmill assembly 70. The power take-off assembly 72 is also interconnected to an auxiliary drive assembly 74' which may be associated with each of the magnetic arrays 30', 32'. Further, supplementary magnetic arrays, schematically represented as 30" and 32", may also be oriented in a somewhat stacked orientation on one or both sides of the treatment area 16. This will further assure the provision of a maximum exposure of generated, moving magnetic fields to a user 12 within the treatment area 16 associated with the frame 14".

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

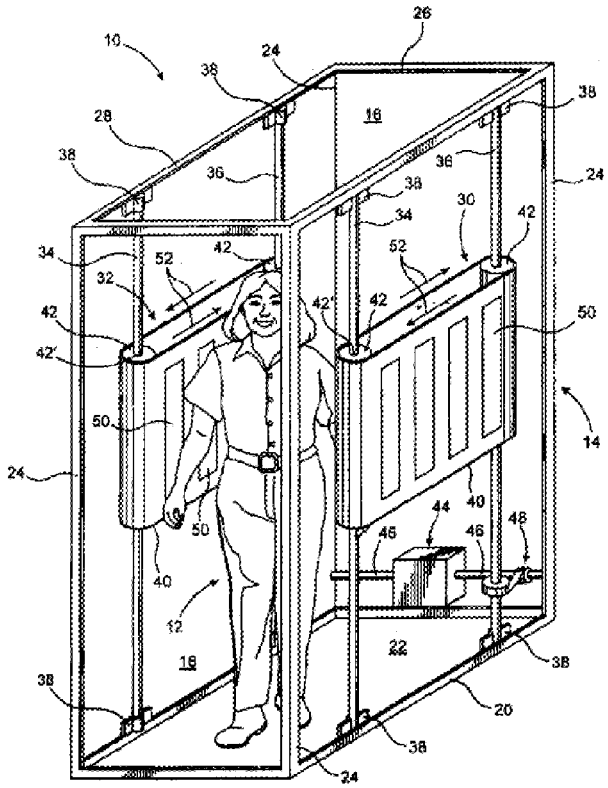

What is claimed is:

1. An assembly structured to expose a user to a therapeutically beneficial magnetic field, said assembly comprising:
    a frame disposed adjacent to and at least partially defining a treatment area,
    said treatment area dimensioned and configured to accommodate the user therein,
    a generating assembly structured and disposed to generate a moving magnetic field which communicates with said treatment area, and
    said generating assembly comprising at least one magnetic array continuously movable in a single direction along a substantially linear path of travel relative to said treatment area; said at least one magnetic array structured to expose said treatment area and the user therein to the moving magnetic field.

2. An assembly as recited in claim 1 wherein said frame and said treatment area are relatively disposed and cooperatively structured to accommodate the user in an upright orientation.

3. An assembly as recited in claim 2 wherein said frame and said treatment area are relatively disposed and cooperatively structured to accommodate the user in a moving orientation.

4. An assembly as recited in claim 3 wherein said frame and said treatment area are relatively disposed and cooperatively structured to accommodate the user in a walking or running orientation.

5. An assembly as recited in claim 2 further comprising a support platform disposed within said treatment area in supporting relation to the user.

6. An assembly as recited in claim 5 wherein said support platform is movable relative to said frame and structured to facilitate movement of the user within said treatment area.

7. An assembly as recited in claim 5 wherein said support platform comprises a treadmill assembly.

8. An assembly as recited in claim 1 wherein said magnetic array comprises a base movable relative to said frame and said treatment area, said base including a plurality of magnets connected thereto and movable therewith.

9. An assembly as recited in claim 8 wherein said plurality of magnets are disposed on said base in predetermined relation to said treatment area, said plurality of magnets cooperatively structured to generate a moving magnetic field passing through said treatment area in a single substantially linear direction and in communicating relation with the user therein.

10. An assembly as recited in claim 1 wherein said generating assembly comprises at least two magnetic arrays each movable relative to and in communication with said treatment area, each of said magnetic arrays disposed to expose the user to a different moving magnetic field.

11. An assembly as recited in claim 10 further comprising a support platform disposed within said treatment area in supporting relation to the user and moveable relative to said frame.

12. An assembly as recited in claim 11 wherein said support platform and at least one of said magnetic arrays are cooperatively structured for at least partially synchronized movement.

13. An assembly as recited in claim 10 wherein each of said magnetic arrays is disposed adjacent a different side of said frame.

14. An assembly as recited in claim 13 wherein said two magnetic arrays are connected to substantially opposite sides of the frame and disposed to generate separate magnetic fields each passing through said treatment area in a single substantially common direction and in communicating relation to the user.

15. An assembly as recited in claim 10 wherein each of said magnetic arrays comprise a base movable relative to said frame and said treatment area, said base including a plurality of magnets connected thereto and movable therewith.

16. An assembly as recited in claim 15 wherein said plurality of magnets on each of said bases are disposed in predetermined relation to said treatment area, each plurality of magnets cooperatively structured to generate a moving magnetic field passing continuously through said treatment area in a single substantially common linear direction and in communicating relation to the user therein.

17. An assembly as recited in claim 15 wherein each of said bases comprise a conveyor movable along a substantially continuous path of travel.

18. An assembly as recited in claim 17 wherein each magnetic array comprises said plurality of magnets disposed in laterally spaced relation to one another on a corresponding one of said bases and along at least a majority of a respective one of said continuous paths of travel.

19. An assembly structured to expose a user to a therapeutically beneficial magnetic field, said assembly comprising:
a frame structured to at least partially define a treatment area,
said treatment area dimensioned and configured to accommodate a user therein,
a generating assembly including a plurality of magnetic arrays each movable relative to said treatment area,
each of said magnetic arrays comprising a plurality of magnets relatively disposed to collectively generate a different movable magnetic field, and
said movable magnetic fields continuously passing through said treatment area in a single, common, linear direction and in communicating relation with the user therein.

20. An assembly as recited in claim 19 wherein said treatment area is dimensioned and configured to accommodate the user in an upright orientation concurrent to generating said movable magnetic fields.

21. An assembly as recited in claim 19 wherein at least two of said plurality of magnetic arrays are disposed on opposite sides of said treatment area.

22. An assembly as recited in claim 19 wherein said frame is disposed in substantially surrounding relation to said treatment area.

23. An assembly as recited in claim 19 further comprising a moveable support platform disposed within said treatment area, said movable support platform structured to moveably support the user in a walking or running orientation thereon.

24. An assembly as recited in claim 19 wherein said frame is mobile and structured to move over a supporting surface concurrently to generation of said moving magnetic fields.

25. An assembly as recited in claim 24 wherein said frame comprises a moveable support assembly structured to travel over the supporting surface and connected in driving relation to said magnetic arrays.

26. An assembly structured to expose a user to a therapeutically beneficial magnetic field, said assembly comprising:
a frame disposed adjacent to and at least partially defining a treatment area,
said treatment area dimensioned and configured to accommodate the user therein in an upright orientation,
a support platform disposed within said treatment area in supporting relation to the user;
said support platform moveable relative to said frame and structured to facilitate movement of the user within said treatment area,
a generating assembly structured and disposed to generate a moving magnetic field which communicates with said treatment area, and
said generating assembly comprising at least one magnetic array continuously moveable in a single linear direction relative to and structured to expose said treatment area and the user therein to the moving magnetic field.

27. An assembly structured to expose a user to a therapeutically beneficial magnetic field, said assembly comprising:
a frame disposed adjacent to and at least partially defining a treatment area,
said treatment area dimensioned and configured to accommodate the user therein,
a generating assembly comprising at least two magnetic arrays each disposed and structured to generate a different moving magnetic field in communication with said treatment area and a user therein, and
each of said magnetic arrays including at least a portion thereof continuously moveable in a single, common direction relative to said treatment area.

28. An assembly as recited in claim 27 wherein said portion of each of said magnetic arrays are structured to move along a different substantially linear path of travel relative to said treatment area.

29. An assembly structured to expose a user to a therapeutically beneficial magnetic field, said assembly comprising:
a frame disposed adjacent to and at least partially defining a treatment area,
said treatment area dimensioned and configured to accommodate the user therein,
a generating assembly structured and disposed to generate a magnetic field which communicates with said treatment area, said generating assembly comprising at least one magnetic array movable relative to and structured to expose said treatment area and the user therein to a moving magnetic field, said frame being mobile and structured to move over a supporting surface concurrently to generation of said moving magnetic field, and said frame comprising a movable support assembly structured to travel over the supporting surface and connected in driving relation to said magnetic array.

30. An assembly as recited in claim 29 wherein a magnetic array is movably mounted on said frame relative to said treatment area and movable with said frame and said treatment area relative to the supporting surface.

31. An assembly as recited in claim 29 wherein said treatment area is movable with said frame, said frame and said generating assembly propelled by a user within said treatment area.

32. An assembly structured to expose a user to a therapeutically beneficial magnetic field, said assembly comprising:

a frame disposed adjacent to and at least partially defining a treatment area, said treatment area dimensioned and configured to accommodate the user therein, a generating assembly structured and disposed to generate a magnetic field which communicates with said treatment area, said generating assembly comprising at least one magnetic array movable relative to and structured to expose said treatment area and the user therein to a moving magnetic field, said magnetic array comprising a base movable relative to said frame and said treatment area, said base including a plurality of magnets connected thereto and movable therewith, and said base comprising a conveyor movable along a substantially continuous path of travel.

33. An assembly as recited in claim 32 wherein said plurality of magnets are disposed in laterally spaced relation to one another on said base and along said continuous path of travel.

* * * * *

UNITED STATES PATENT AND TRADEMARK OFFICE
CERTIFICATE OF CORRECTION

PATENT NO.        : 6,971,983 B1                                         Page 1 of 3
APPLICATION NO.   : 10/885158
DATED             : December 6, 2005
INVENTOR(S)       : Humberto Cancio It is certified that error appears in the above-identified patent and that said Letters Patent is hereby corrected as shown below:

The title page showing the illustrative figure should be deleted to be replaced with the attached title page.

Drawing sheets, consisting of fig. 1, should be deleted to be replaced with the drawing sheet, consisting of fig. 1, as shown on the attached page.

Signed and Sealed this

Eighth Day of January, 2008

JON W. DUDAS
*Director of the United States Patent and Trademark Office*

(12) United States Patent
Cancio

(10) Patent No.: US 6,971,983 B1
(45) Date of Patent: Dec. 6, 2005

(54) THERAPEUTICALLY BENEFICIAL MOVABLE MAGNETIC FIELDS

(76) Inventor: Humberto Cancio, 7731 SW. 32 St., Miami, FL (US) 33155

(*) Notice: Subject to any disclaimer, the term of this patent is extended or adjusted under 35 U.S.C. 154(b) by 0 days.

(21) Appl. No.: 10/885,158

(22) Filed: Jul. 6, 2004

(51) Int. Cl.$^7$ ............................................. A61N 2/00
(52) U.S. Cl. ............................................. 600/9
(58) Field of Search ............................... 600/9–15

(56) References Cited

U.S. PATENT DOCUMENTS

| | | | |
|---|---|---|---|
| 4,537,181 A * | 8/1985 | Shalhoob et al. | 600/9 |
| 4,727,857 A * | 3/1988 | Horl | 600/15 |
| 4,744,350 A | 5/1988 | Sato | |
| 5,084,003 A | 1/1992 | Susic | |
| 5,453,073 A * | 9/1995 | Markoll | 600/14 |
| 5,632,720 A | 5/1997 | Kleitz | |
| 5,667,469 A * | 9/1997 | Zhang et al. | 600/9 |
| 5,788,624 A | 8/1998 | Lu et al. | |
| 5,817,000 A | 10/1998 | Souder | |
| 6,001,055 A | 12/1999 | Souder | |
| 6,231,497 B1 | 5/2001 | Souder | |
| 6,663,557 B2 * | 12/2003 | Werny | 600/15 |
| 2004/0097781 A1 * | 5/2004 | Ichikawa et al. | 600/9 |

* cited by examiner

Primary Examiner—John P. Lacyk
(74) Attorney, Agent, or Firm—Malloy & Malloy, P.A.

(57) ABSTRACT

The present invention relates to a therapeutically beneficial assembly utilizing one or more moveable magnetic fields passing through a treatment area, which is dimensioned and configured to accommodate a user in a standing, walking and/or running orientation therein. A generating assembly comprises at least one but preferably at least two magnetic arrays each mounted in moveable relation to the treatment area and comprising a conveyor-like base having a plurality of magnets connected thereto and moveable therewith. The plurality of magnets of each of said magnetic array are disposed to generate a different magnetic field moveable through said treatment area such that the user therein is exposed to the one or more moveable magnetic fields.

33 Claims, 3 Drawing Sheets